US 7,417,742 B2

(12) United States Patent
Ozcan et al.

(10) Patent No.: US 7,417,742 B2
(45) Date of Patent: Aug. 26, 2008

(54) METHOD FOR ESTIMATING THE OPTICAL NONLINEARITY OF A MATERIAL

(75) Inventors: Aydogan Ozcan, Menlo Park, CA (US); Michel J. F. Diggonet, Palo Alto, CA (US); Gordon S. Kingo, Stanford, CA (US)

(73) Assignee: The Board of Trustess of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 11/841,587

(22) Filed: Aug. 20, 2007

(65) Prior Publication Data

US 2007/0282569 A1    Dec. 6, 2007

Related U.S. Application Data

(63) Continuation of application No. 10/996,166, filed on Nov. 23, 2004, now Pat. No. 7,259,868.

(60) Provisional application No. 60/571,659, filed on May 15, 2004, provisional application No. 60/524,792, filed on Nov. 25, 2003.

(51) Int. Cl.
*G01B 9/02* (2006.01)
(52) U.S. Cl. ..................................... 356/511
(58) Field of Classification Search ................. 356/489, 356/495, 511, 512
See application file for complete search history.

(56) References Cited

U.S. PATENT DOCUMENTS

| 3,880,630 | A | 4/1975 | Izawa |
| 4,674,824 | A | 6/1987 | Goodman et al. |
| 4,778,236 | A | 10/1988 | Miyawaki |
| 4,792,230 | A | 12/1988 | Naganuma et al. |
| 4,985,178 | A | 1/1991 | Tam |
| 5,086,239 | A | 2/1992 | Wang |
| 5,194,918 | A | 3/1993 | Kino et al. |
| 5,220,451 | A | 6/1993 | Gotoh et al. |

(Continued)

FOREIGN PATENT DOCUMENTS

JP    2000-329618    11/2000

(Continued)

OTHER PUBLICATIONS

Alley, T. G., et al., "Space charge dynamics in thermally poled fused silica," *Journal of Non-Crystalline Solids*, vol. 242, 1998, pp. 165-176.

(Continued)

*Primary Examiner*—Patrick J Connolly
(74) *Attorney, Agent, or Firm*—Knobbe Martens Olson & Bear LLP

(57) ABSTRACT

A method estimates a nonlinearity profile of a material. The method includes providing a magnitude of a transform of a measured nonlinearity profile measured from the material. The method further includes providing an estimated phase term of the transform of the measured nonlinearity profile. The method further includes multiplying the magnitude and the estimated phase term to generate an estimated transform. The method further includes calculating an inverse transform of the estimated transform. The method further includes calculating a real component of the inverse transform to generate an estimated nonlinearity profile.

35 Claims, 12 Drawing Sheets

U.S. PATENT DOCUMENTS

| | | | |
|---|---|---|---|
| 5,239,407 | A | 8/1993 | Brueck et al. |
| 5,247,601 | A | 9/1993 | Myers et al. |
| 5,262,890 | A | 11/1993 | Berkovic et al. |
| 5,309,532 | A | 5/1994 | Chang et al. |
| 5,317,147 | A | 5/1994 | Dandliker et al. |
| 5,368,782 | A | 11/1994 | Gotoh et al. |
| 5,420,717 | A | 5/1995 | Tabata |
| 5,434,699 | A | 7/1995 | Berkovic et al. |
| 5,481,636 | A | 1/1996 | Fukuda et al. |
| 5,523,840 | A | 6/1996 | Nishizawa et al. |
| 5,530,544 | A | 6/1996 | Trebino et al. |
| 5,615,041 | A | 3/1997 | Field et al. |
| 5,737,116 | A | 4/1998 | Kadowaki et al. |
| 5,986,798 | A | 11/1999 | Karlsson et al. |
| 6,043,884 | A | 3/2000 | Curbelo |
| 6,456,380 | B1 | 9/2002 | Naganuma |
| 6,479,822 | B1 | 11/2002 | Nelson et al. |
| 6,608,690 | B2* | 8/2003 | Niu et al. ............... 356/635 |
| 6,650,466 | B1 | 11/2003 | Wise et al. |
| 6,728,273 | B2 | 4/2004 | Perry |
| 6,856,393 | B2* | 2/2005 | Ozcan et al. ............ 356/432 |
| 7,050,169 | B2* | 5/2006 | Ozcan et al. ............ 356/432 |
| 7,148,970 | B2* | 12/2006 | de Boer ................. 356/497 |
| 7,236,246 | B2* | 6/2007 | Ozcan et al. ............ 356/432 |
| 7,236,247 | B2* | 6/2007 | Ozcan et al. ............ 356/432 |
| 7,259,868 | B2* | 8/2007 | Ozcan et al. ............ 356/511 |
| 7,271,918 | B2* | 9/2007 | De Groot et al. ........ 356/511 |
| 2004/0036880 | A1* | 2/2004 | Ozcan et al. ............ 356/432 |
| 2004/0044714 | A1* | 3/2004 | Ozcan et al. ............ 708/404 |
| 2004/0133614 | A1* | 7/2004 | Ozcan et al. ............ 708/404 |
| 2004/0189999 | A1* | 9/2004 | De Groot et al. ........ 356/497 |
| 2005/0073692 | A1* | 4/2005 | De Groot et al. ........ 356/497 |
| 2005/0111002 | A1* | 5/2005 | Ozcan et al. ............ 356/432 |
| 2006/0132783 | A1* | 6/2006 | Ozcan et al. ............ 356/432 |
| 2006/0139645 | A1* | 6/2006 | Ozcan et al. ............ 356/432 |
| 2007/0025432 | A1* | 2/2007 | Ozcan et al. ............ 356/224 |
| 2007/0025638 | A1* | 2/2007 | Ozcan et al. ............ 382/280 |
| 2007/0027689 | A1* | 2/2007 | Ozcan et al. ............ 704/258 |
| 2007/0050162 | A1* | 3/2007 | Ozcan et al. ............. 702/77 |
| 2007/0055466 | A1* | 3/2007 | Ozcan et al. ............. 702/72 |
| 2007/0097380 | A1* | 5/2007 | De Groot et al. ........ 356/511 |
| 2007/0211253 | A1 | 9/2007 | Ozcan et al. |

FOREIGN PATENT DOCUMENTS

| | | |
|---|---|---|
| JP | 2001-083015 | 3/2001 |
| WO | PCT/US03/26311 | 8/2003 |
| WO | PCT/US2004/039320 | 6/2005 |

OTHER PUBLICATIONS

Bonfrate, G., et al., "Parametric fluorescence in periodically poled silica fibers," *Applied Physics Letters*, vol. 75, No. 16, Oct. 18, 1999, pp. 2356-2358.

Faccio, D., et al., "Dynamics of the second-order nonlinearity in thermally poled silica glass," *Applied Physics Letters*, vol. 79, No. 17, Oct. 22, 2001, pp. 2687-2689.

Fienup, J.R., "Phase retrieval algorithms: a comparison," *Applied Optics*, vol. 21, No. 15, Aug. 1, 1982, pp. 2758-2769.

Ferreira, P. J. S. G., "Interpolation and the Discrete Papoulis-Gerchberg Algorithm," *IEEE Transactions on Signal Processing*, vol. 42, No. 10, Oct. 1994, pp. 2596-2606.

Fienup, J.R., "Reconstruction of an object from the modulus of its Fourier transform," *Optics Letters*, vol. 3, No. 1, Jul. 1978, pp. 27-29.

Fisher, R. A., et al., "Transient analysis of Kerr-like phase conjugators using frequency-domain techniques," *Physical Review A*, vol. 23, No. 6, Jun. 1981, pp. 3071-3083.

Kashyap, R., et al., Phase-matched second harmonic generation by periodic poling of fused silica, *Applied Physics Letters*, vol. 64, No. 11, Mar. 14, 1994, pp. 1332-1334.

Kazansky, P.G., et al., "Thermally poled silica glass: Laser induced pressure pulse probe of charge distribution," *Applied Physics Letters*, vol. 68, No. 2, Jan. 8, 1996, pp. 269-271.

Liu, A. C., et al., "Advances in the measurement of the poled silica nonlinear profile," *SPIE*, vol. 3542, Nov. 1998, pp. 115-119.

Maker, et al., "Effects of Dispersion and Focusing on the Production of Optical Harmonics," *Physical Review Letters*, vol. 8, No. 1, Jan. 1, 1962, pp. 21-22.

Millane, R. P., "Analytic Properties of the Hartley Transform and their Implications," *Proceedings Of The IEEE*, vol. 82, No. 3, Mar. 1994, pp. 413-428.

Miller, D.A.B., "Time reversal of optical pulses by four-wave mixing," *Optics Letters*, vol. 5, No. 7, Jul. 1980, pp. 300-302.

Myers, R. A., et al., "Large second-order nonlinearity in poled fused silica," *Optics Letters*, vol. 16, No. 22, Nov. 15, 1991, pp. 1732-1734.

Nakajima, N., "Reconstruction of a real function from its Hartley-transform intensity," *J. Opt. Soc. Am. A.*, vol. 5, No. 6, Jun. 1988, pp. 858-863.

Ozcan, A., et al., "A simple post-processing technique to improve the retrieval accuracy of second-order nonlinearity profiles," Edward L. Ginzton Laboratory: Stanford University, Stanford, California 94305; © 2004 Optical Society of America, 2 pages.

Ozcan, A., et al., "Cylinder-assisted Maker-fringe Technique," *Electronics Letters*, vol. 39, No. 25, 11th Dec. 2003, 2 pages.

Ozcan, A., et al., "Improved Fourier transform technique to determine second-order optical nonlinearity profiles," Edward L. Ginzton Laboratory: Stanford University, Stanford, California 94305; © 2003 Optical Society of America, 3 pages.

Ozcan, A., et al., "Improved technique to determine second-order optical nonlinearity profiles using two different samples," *Applied Physics Letters*, vol. 84, No. 5, Feb. 2, 2004, pp. 681-683.

Ozcan, A., et al., "Inverse Fourier transform technique to determine second-order optical nonlinearity spatial profiles," *Applied Physics Letters*, vol. 82, No. 9, Mar. 3, 2002, pp. 1362-1364.

Ozcan, A., et al., Erratum: "Inverse Fourier transform technique to determine second-order optical nonlinearity spatial profiles," *Applied Physics Letters*, vol. 83, No. 8, Aug. 25, 2003, p. 1679.

Ozcan, A., et al., "Post-processing of the second-order optical nonlinearity profile of thin films," Edward L. Ginzton Laboratory: Stanford University, Stanford, California 94305; © Optical Society of America, 2 pages.

Ozcan, A., et al., "Simplified inverse Fourier transform technique to measure optical nonlinearity profiles using reference sample," *Electronics Letters*, vol. 40, No. 9, Apr. 29, 2004, 2 pages.

Peri, David, "Optical implementation of a phase retrieval algorithm," *Applied Optics*, vol. 26, No. 9, May 1, 1987, pp. 1782-1785.

Pureur, D., et al., "Absolute measurement of the second-order nonlinearity profile in poled silica," *Optics Letters*, vol. 23, No. 8, Apr. 15, 1998, pp. 588-590.

Quatieri, T. F, Jr., et al., "Iterative Techniques for Minimum Phase Signal Reconstruction from Phase or Magnitude," *IEEE Trans. Acoust., Speech, and Signal Processing*, vol. ASSP-29, No. 6, Dec. 1981, pp. 1187-1193.

Qui, M., et al., "Double fitting of Marker fringes to characterize near-surface and bulk second-order nonlinearities in poled silica," *Applied Physics Letters*, vol. 76, No. 23, Jun. 5, 2000, pp. 3346-3348.

Qui, M., et l., Erratum:_"Double fitting of Marker fringes to characterize near-surface and bulk second-order nonlinearities in poled silica," *Applied Physics Letters*, vol. 77, No. 23, Dec. 4, 2000, p. 3863.

Quiquempois, Y., et al., "Localisation of the induced second-order non-linearity within Infrasil and Suprasil thermally poled glasses," *Optics Communications*, vol. 176, Apr. 1, 2000, pp. 479-487.

Rosenthal, A., et al., "Inverse Scattering Algorithm for Reconstructing Strongly Reflecting Fiber Bragg Gratings," *IEEE Journal of Quantum Electronics*, vol. 39, No. 8, Aug. 2003, pp. 1018-1026.

Sun, P.C., et al., "Femtosecond pulse imaging: ultrafast optical oscilloscope," *J. Opt. Soc. Am. A*, vol. 14, No. 5, May 1997, pp. 1159-1170.

Watanabe, S., et al., "Compensation of Chromatic Dispersion in a Single-Mode Fiber by Optical Phase Conjugation," *IEEE Photonics Technology Letters*, vol. 5, No. 1, Jan. 1993, pp. 92-95.

Weiner, A. M., et al., "Femtosecond Pulse Shaping for Synthesis, Processing, and Time-to-Space Conversion of Ultrafast Optical Waveforms," *IEEE Journal of Selected Topics in Quantum Electronics*, vol. 4, No. 2, Mar./Apr. 1998, pp. 317-331.

Weiner, A. M., et al., "Femtosecond Spectral Holography," *IEEE Journal Of Quantum Electronics*, vol. 28, No. 10, Oct. 1992, pp. 2251-2256.

Xu, Zhiling, et al., "Nonuniform bulk second-order optical nonlinearity in $PbO/B_2O_3$ glass," *Applied Physics Letters*, vol. 77, No. 1, Jul. 3, 2000, pp. 70-72.

Yariv, A., et al., "Compensation for channel dispersion by nonlinear optical phase conjugation," *Optics Letters*, vol. 4, No. 2, Feb. 1979, pp. 52-54.

* cited by examiner

METHOD FOR ESTIMATING THE OPTICAL NONLINEARITY OF A MATERIAL

CLAIM OF PRIORITY

This application is a continuation of U.S. patent application Ser. No. 10/996,166, filed Nov. 23, 2004, now U.S. Pat. No. 7,259,868 incorporated in its entirety by reference herein, and which claims the benefit of U.S. Provisional Application No. 60/524,792, filed Nov. 25, 2003 and U.S. Provisional Application No. 60/571,659, filed May 15, 2004, both of which are incorporated in their entireties by reference herein.

BACKGROUND OF THE INVENTION

1. Field of the Invention

The present application relates generally to methods of estimating the optical nonlinearity profile of a material.

2. Description of the Related Art

In thermal poling of silica, a silica wafer is heated (e.g., to approximately 270 degrees Celsius) while an external voltage (e.g., approximately 5 kilovolts) is applied to the wafer. This process induces a second-order nonlinear region under the anode electrode, and this nonlinear region does not decay upon cooling the wafer to room temperature and removing the applied voltage. The depth profile of this induced nonlinear region is often non-uniform and can have a variety of functional forms. The depth profile is a key parameter for understanding the theory of poling, improving the strength and/or width of the induced nonlinear region, and for the design of poled electro-optics devices.

The Maker fringe technique, as described by P. D. Maker et al. in "Effects of dispersion and focusing on the production of optical harmonics," Physical Review Letters, Vol. 8, pp. 21-22 (1962), is a method for obtaining information regarding the nonlinearity profile of a material. It involves focusing a laser beam onto the material (e.g., an optically nonlinear wafer) and measuring the generated second-harmonic (SH) power as a function of the laser incidence angle ($\theta$). The dependence of the SH power on $\theta$ is known as the Maker fringe (MF) curve, and is proportional to the square of the Fourier transform magnitude of the nonlinearity profile $d(z)$. For thin films under study, z is in the direction perpendicular to the thin film. Consequently, in principle, $d(z)$ is retrievable by inverting this Fourier transform. However, $d(z)$ cannot be retrieved without the knowledge of the phase of this Fourier transform, which is not provided by the measurement of the MF curve. In the past, this limitation has been mitigated by assuming that $d(z)$ has a given shape (e.g., Gaussian) and using a fitting process, but this approach fails to provide the actual nonlinearity profile $d(z)$.

Recently, this problem was solved by introducing a new family of inverse Fourier Transform (IFT) techniques that involve measuring the MF curves of sandwich structures formed by mating two optically nonlinear samples. As a result of interference between the samples, these MF curves contain the phase of the Fourier transform of the nonlinearity profiles, and the profiles can be recovered uniquely. Examples of these IFT techniques are described in U.S. patent application Ser. No. 10/357,275, filed Jan. 31, 2003, U.S. patent application Ser. No. 10/378,591, filed Mar. 3, 2003, and U.S. patent application Ser. No. 10/645,331, filed Aug. 21, 2003. These IFT techniques are further described by A. Ozcan, M. J. F. Digonnet, and G. S. Kino, "Inverse Fourier Transform technique to determine second-order optical nonlinearity spatial profiles," *Applied Physics Letters*, Vol. 82, pp. 1362-1364 (2003) [Ozcan I]; A. Ozcan, M. J. F. Digonnet, and G. S. Kino, "Erratum: Inverse Fourier Transform technique to determine second-order optical nonlinearity spatial profiles," *Applied Physics Letters*, Vol. 83, p. 1679 (2003) [Ozcan II]; A. Ozcan, M. J. F. Digonnet, and G. S. Kino, "Improved technique to determine second-order optical nonlinearity profiles using two different samples," *Applied Physics Letters*, Vol. 84, No. 5, pp. 681-683 (Feb. 2, 2004) [Ozcan III]; A. Ozcan, M. J. F. Digonnet, and G. S. Kino, "Simplified inverse Fourier transform technique to measure optical nonlinearity profiles using a reference sample," *Electronics Letters*, Vol. 40, No. 9, pp. 551-552 (Apr. 29, 2004) [Ozcan IV].

SUMMARY OF THE INVENTION

In certain embodiments, a method estimates a nonlinearity profile of a material. The method comprises providing a magnitude of a transform of a measured nonlinearity profile measured from the material. The method further comprises providing an estimated phase term of the transform of the measured nonlinearity profile. The method further comprises multiplying the magnitude and the estimated phase term to generate an estimated transform. The method further comprises calculating an inverse transform of the estimated transform. The method further comprises calculating a real component of the inverse transform to generate an estimated nonlinearity profile.

In certain embodiments, a method improves the accuracy of a measured nonlinearity profile of a material. The method comprises providing the measured nonlinearity profile of the material in an operation (a). The method further comprises calculating a magnitude of a transform of the measured nonlinearity profile in an operation (b). The method further comprises providing an estimated phase term of the transform of the measured nonlinearity profile in an operation (c). The method further comprises multiplying the magnitude and the estimated phase term to generate an estimated transform in an operation (d). The method further comprises calculating an inverse transform of the estimated transform in an operation (e). The method further comprises calculating a real component of the inverse transform to generate an estimated nonlinearity profile in an operation (f). The method further comprises calculating a transform of the estimated nonlinearity profile in an operation (g). The method further comprises calculating a calculated phase term of the transform of the estimated nonlinearity profile in an operation (h). The method further comprises using the calculated phase term of operation (h) as the estimated phase term of operation (d) in an operation (i). The method further comprises iteratively repeating operations (d)-(i) until the estimated nonlinearity profile reaches convergence.

In certain embodiments, a computer-readable medium has instructions stored thereon which cause a general-purpose computer to perform a method of estimating a nonlinearity profile of a material. The method comprises estimating an estimated phase term of a transform of a measured nonlinearity profile measured from the material. The method further comprises multiplying a magnitude of the transform of a measured nonlinearity profile measured from the material and the estimated phase term to generate an estimated transform. The method further comprises calculating an inverse transform of the estimated transform. The method further comprises calculating a real component of the inverse transform to generate an estimated nonlinearity profile.

In certain embodiments, a computer system comprises means for estimating an estimated phase term of a transform of a measured nonlinearity profile measured from the material. The computer system further comprises means for multiplying a magnitude of the transform of a measured nonlinearity profile measured from the material and the estimated phase term to generate an estimated transform. The computer system further comprises means for calculating an inverse transform of the estimated transform. The computer system further comprises means for calculating a real component of the inverse transform to generate an estimated nonlinearity profile.

DETAILED DESCRIPTION OF THE PREFERRED EMBODIMENT

Figure 1:
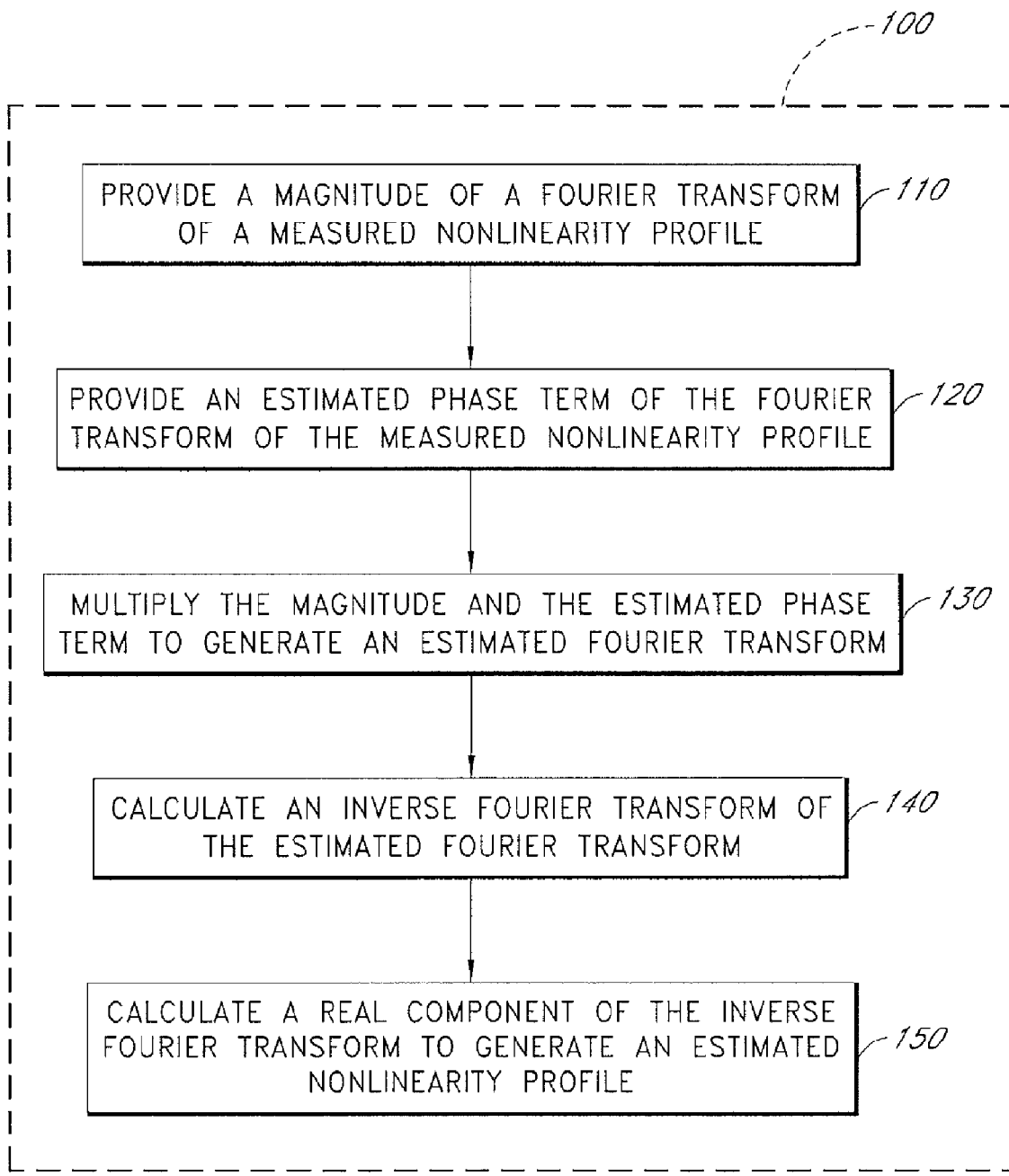
FIG. 1 is a flowchart of an exemplary embodiment of a method of determining a nonlinearity profile of a material.

Because of limitations inherent to the basic Maker fringe (MF) technique (e.g., the inability to measure the entire Fourier transform spectrum or errors introduced by the finite divergence of the laser beam), the recovered nonlinearity profile exhibits a certain amount of error. As described herein, a simple and fast post-processing technique can be applied to the recovered nonlinearity profile to correct some of these errors and improve the profile accuracy. This technique is broadly applicable to any Fourier transform technique that can retrieve the nonlinearity profile of a material.

Certain embodiments described herein are advantageously used to process the measured MF curve of an optically nonlinear sample to retrieve the second-order nonlinearity spatial profile d(z) of the sample. In certain embodiments, the second-order nonlinearity profile d(z) is that of a thin-film material or a surface, and the spatial dimension z is generally perpendicular to the thin-film material or the surface. Certain embodiments are particularly accurate when retrieving a second-order nonlinearity profile that exhibits one or two dominant peaks. Examples of materials for which certain embodiments of the methods described herein are useful include, but are not limited to, optically nonlinear films of crystalline or organic materials (e.g., hundreds of microns thick), and poled silica.

Certain embodiments of the methods described herein utilize an algorithm described by J. R. Fienup in "Reconstruction of an object from the modulus of its Fourier transform," *Optics Letters*, Vol. 3, 27-29 (1978). This algorithm (referred to as "the Fienup algorithm" herein) is an error-reduction algorithm that involves using a known (e.g., measured) Fourier transform magnitude of an unknown function g(t), together with known properties of this function (e.g., that it is a real function or a causal function), to correct an initial guess of g(t). In certain embodiments, this correction is done iteratively.

Certain embodiments described herein are useful in computer-implemented analysis of the nonlinearity profiles of materials. The general purpose computers used for this purpose can take a wide variety of forms, including network servers, workstations, personal computers, mainframe computers and the like. The code which configures the computer to perform the analysis is typically provided to the user on a computer-readable medium, such as a CD-ROM. The code may also be downloaded by a user from a network server which is part of a local-area network (LAN) or a wide-area network (WAN), such as the Internet.

The general-purpose computer running the software will typically include one or more input devices, such as a mouse, trackball, touchpad, and/or keyboard, a display, and computer-readable memory media, such as random-access memory (RAM) integrated circuits and a hard-disk drive. It will be appreciated that one or more portions, or all of the code may be remote from the user and, for example, resident on a network resource, such as a LAN server, Internet server, network storage device, etc. In typical embodiments, the software receives as an input a variety of information concerning the material (e.g., structural information, dimensions, previously-measured nonlinearity profiles, previously-measured Maker-fringe spectra).

FIG. 1 is a flowchart of an exemplary embodiment of a method 100 of determining an optical nonlinearity profile of a material. The method 100 comprises providing a magnitude $|D_M(f)|$ of a Fourier transform $D_M(f)$ of a nonlinearity profile $d_M(z)$ measured from the material in an operational block 110. As used herein, when used as a functional variable, z denotes spatial dimension and f denotes spatial frequency. The method 100 further comprises providing an estimated phase term $\exp[j\phi_E(f)]$ of the Fourier transform $D_M(f)$ of the measured nonlinearity profile $d_M(z)$ in an operational block 120. The method 100 further comprises multiplying the magnitude $|D_M(f)|$ and the estimated phase term $\exp[j\phi_E(f)]$ to generate an estimated Fourier transform D'(f) in an operational block 130. The method 100 further comprises calculating an inverse Fourier transform of the estimated Fourier transform D'(f) in an operational block 140. The method 100 further comprises calculating a real component of the inverse Fourier transform to generate an estimated nonlinearity profile d'(z) in an operational block 150.

In certain embodiments, providing the magnitude $|D_M(f)|$ of the Fourier transform $D_M(f)$ in the operational block 110 comprises measuring the MF spectrum of the sample. For example, in certain such embodiments, a single MF spectrum is measured from the material, and the measured MF spectrum then provides the magnitude $|D_M(f)|$ of the measured nonlinearity profile $d_M(z)$. In other embodiments, a previously-measured MF spectrum is provided, thereby providing the magnitude $|D_M(f)|$.

Figure 2:
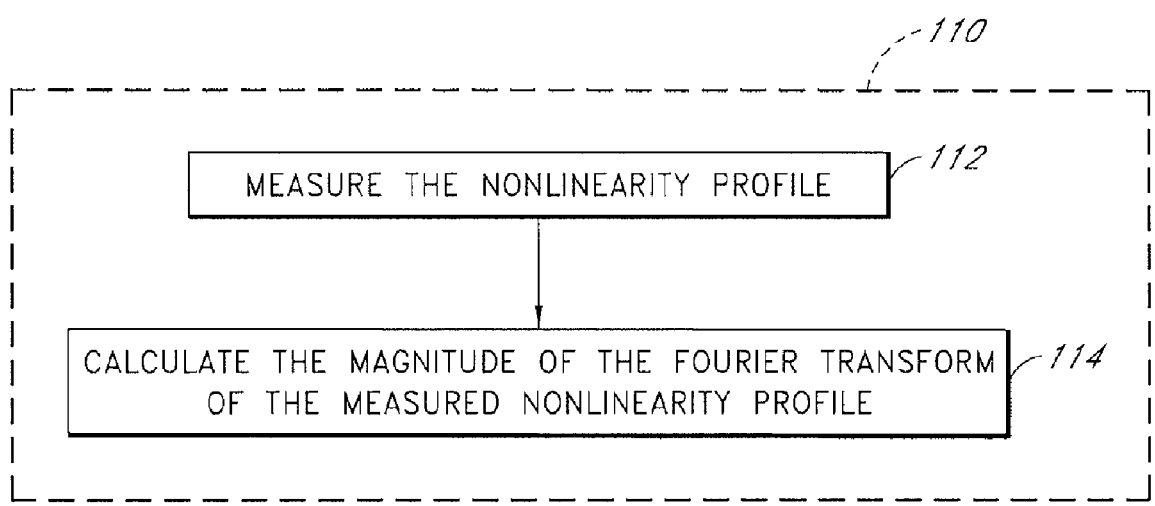
FIG. 2 is a flowchart of a process of providing a magnitude of a Fourier transform of a measured nonlinearity profile in accordance with certain embodiments described herein.

In other embodiments, as shown by the flowchart of FIG. 2, the operation of providing the magnitude $|D_M(f)|$ of the Fourier transform $D_M(f)$ of the measured optical nonlinearity profile $d_M(z)$ comprises measuring the nonlinearity profile $d_M(z)$ in an operational block 112. In certain embodiments, the measured nonlinearity profile $d_M(z)$ is measured by one of the IFT techniques described by U.S. patent application Ser. Nos. 10/357,275, 10/378,591, or 10/645,331. Certain such IFT techniques utilize multiple MF curves which are measured from sandwiched structures which include the material to derive the measured nonlinearity profile of the material. Other techniques for measuring the measured nonlinearity profile $d_M(z)$ are used in other embodiments. In an operational block 114, the magnitude $|D_M(f)|$ of the Fourier transform $D_M(f)$ of the measured nonlinearity profile $d_M(z)$ is calculated.

In certain embodiments, although the measurement of the MF curve of a single sample provides the magnitude $|D_M(f)|$ of the Fourier transform $D_M(f)$, the measurement of the MF curve does not provide the phase term $\exp[j\phi(f)]$ of the Fourier transform $D_M(f)$. In certain embodiments, in the operational block 120, an estimated phase term $\exp[j\phi_E(f)]$ of the Fourier transform $D_M(f)$ is provided. In certain embodiments in which the method 100 is used iteratively, the choice of the initial estimated phase term $\exp[j\phi_E(f)]$ does not strongly impact the convergence of the method. Therefore, in certain such embodiments, the initial estimated phase term is selected to be $\exp[j\phi_E(f)]=1$. In certain other embodiments that utilize an IFT technique that provides a measured phase term $\exp[j\phi_M(f)]$ of the Fourier transform $D_M(f)$, the estimated phase term is selected to be the measured phase term $\exp[j\phi_M(f)]$.

In the operational block 130, the magnitude $|D_M(f)|$ and the estimated phase term $\exp[\phi_E(f)]$ are multiplied together to generate an estimated Fourier transform. In certain embodiments, the estimated Fourier transform $|D_M(f)|\exp[j\phi_E(f)]$ is a complex quantity which is calculated numerically.

In the operational block 140, the inverse Fourier transform of the estimated Fourier transform $|D_M(f)|\exp[j\phi_E(f)]$ is calculated. In certain embodiments, in the operational block 150, a real component of the inverse Fourier transform of the estimated Fourier transform is calculated to generate an estimated nonlinearity profile d'(z). For example, in certain embodiments, when determining the nonlinearity profile of a poled silica sample, the estimated nonlinearity profile d'(z) is a real and causal function. In certain such embodiments, the real component of the inverse Fourier transform is calculated by setting d'(z)=0 for z<0, where z=0 defines the edge of the poled silica sample, and the real portion of the inverse Fourier transform in the region z>0 is used as the estimated nonlinearity profile d'(z).

Figure 3:
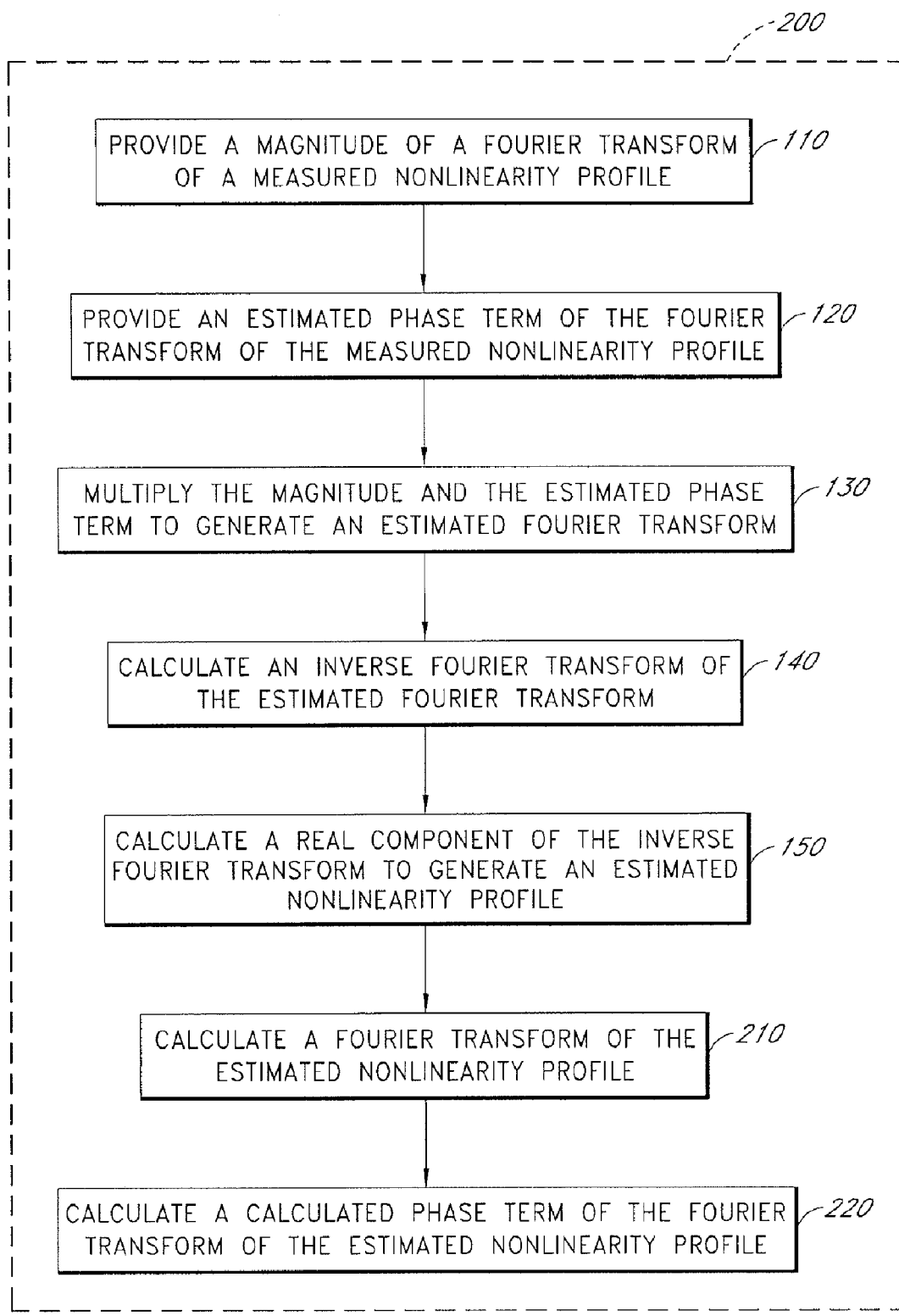
FIG. 3 is a flowchart of another exemplary embodiment of a method of determining a nonlinearity profile of a material.

FIG. 3 is a flowchart of another exemplary embodiment of a method 200 of determining an optical nonlinearity profile for a material in accordance with embodiments described herein. The method 200 comprises the operational blocks 110, 120, 130, 140, and 150, as described herein. The method 200 further comprises calculating a Fourier transform D'(f) of the estimated nonlinearity profile d'(z) in an operational block 210. The method 200 further comprises calculating a phase term $\exp[j\phi_C(f)]$ of the Fourier transform D'(f) of the estimated nonlinearity profile d'(z) in an operational block 220.

In certain embodiments, the Fourier transform D'(f) of the estimated nonlinearity profile d'(z) is calculated numerically in the operational block 210. In certain embodiments, the calculated phase term $\exp[j\phi_C(f)]$ of this Fourier transform D'(f) of the estimated nonlinearity profile d'(z) is calculated numerically in the operational block 220.

Figure 4:
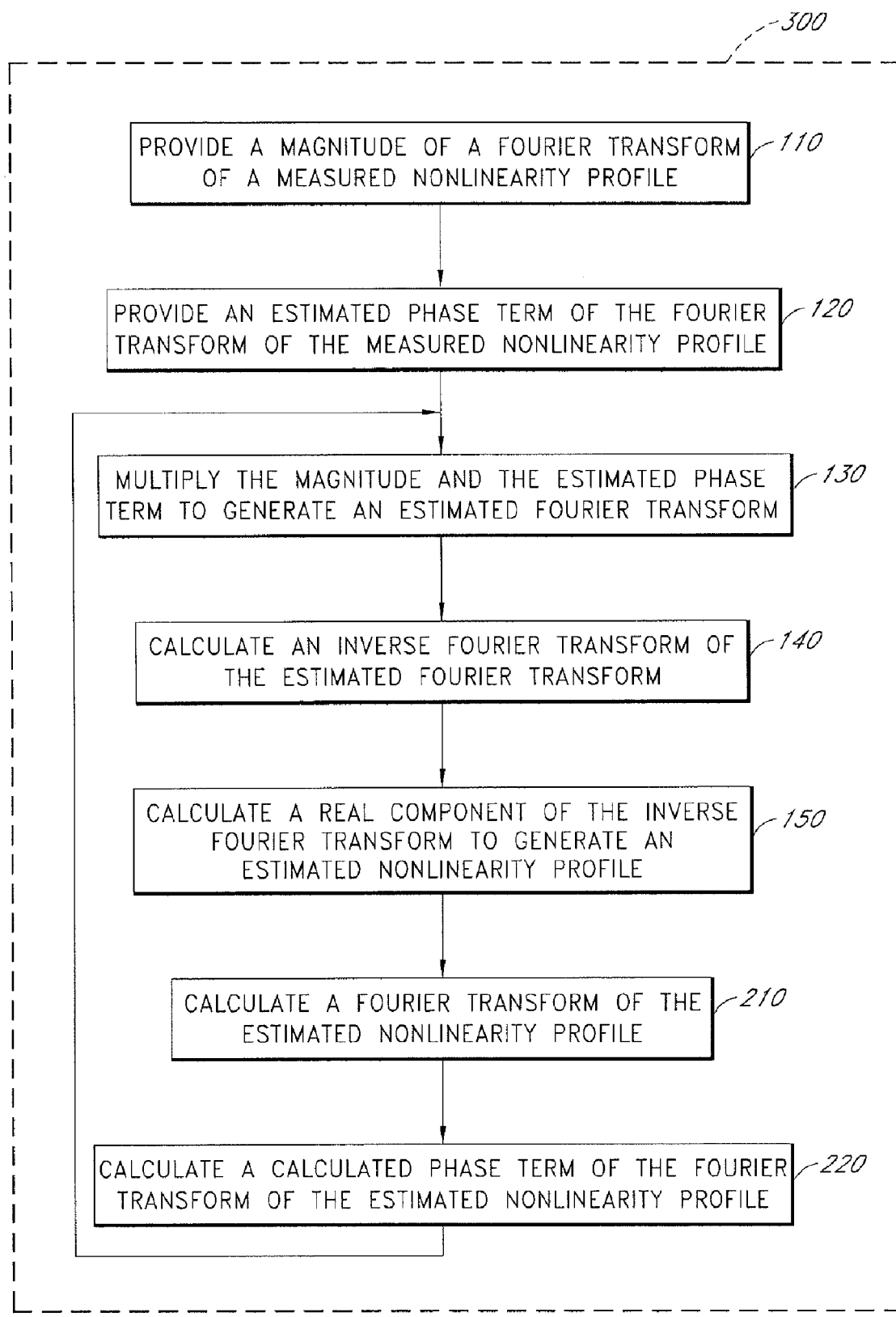
FIG. 4 is a flowchart of another exemplary embodiment of an iterative method of determining a nonlinearity profile of a material.

FIG. 4 is a flowchart of another exemplary embodiment of a method 300 of determining an optical nonlinearity profile of a material in accordance with embodiments described herein. The method 300 comprises the operational blocks 110, 120, 130, 140, 150, 210, and 220, as described herein. The method 300 further comprises using the calculated phase term $\exp[j\phi_C(f)]$ as the estimated phase term $\exp[j\phi_E(f)]$ in the operational block 130 and repeating the operational blocks 130, 140, 150, 210, and 220. This repeat operation is denoted in FIG. 4 by the arrow 310. In certain such embodiments, the calculated phase term $\exp[j\phi_C(f)]$ provides a new estimate for the missing phase term of the nonlinearity profile of the material. The resulting estimated Fourier transform of the operational block 130 is the product of a measured magnitude $|D_M(f)|$ of the Fourier transform of the material and a calculated estimated phase term $\exp[j\phi_C(f)]$. By repeating the operational blocks 130, 140, 150, 210, and 220, a second estimated nonlinearity profile and a second estimated phase term are generated.

In certain embodiments, the operational blocks 130, 140, 150, 210, 220 as shown in FIG. 4 are iteratively repeated a number of times. In certain such embodiments, the iterations are performed until the resulting estimated nonlinearity profile converges. Convergence is reached in certain embodiments when the average difference between the estimated nonlinearity profiles obtained after two consecutive iterations is less than a predetermined value (e.g., 1% of the estimated nonlinearity profile of the iteration). In other embodiments, the iterations are performed a predetermined number of times (e.g., 100 times) rather than determining the differences between successive iterations. After a number of iterations, certain embodiments yield an estimated phase term which is a more accurate estimate of the actual phase term of the Fourier transform of the actual nonlinearity profile of the material than is the initial estimated phase term. In addition, after a number of iterations, certain embodiments yield an estimated nonlinearity profile d'(z) which is a more accurate estimate of the actual nonlinearity profile of the material than is the originally measured nonlinearity profile $d_M(z)$.

Figure 5:
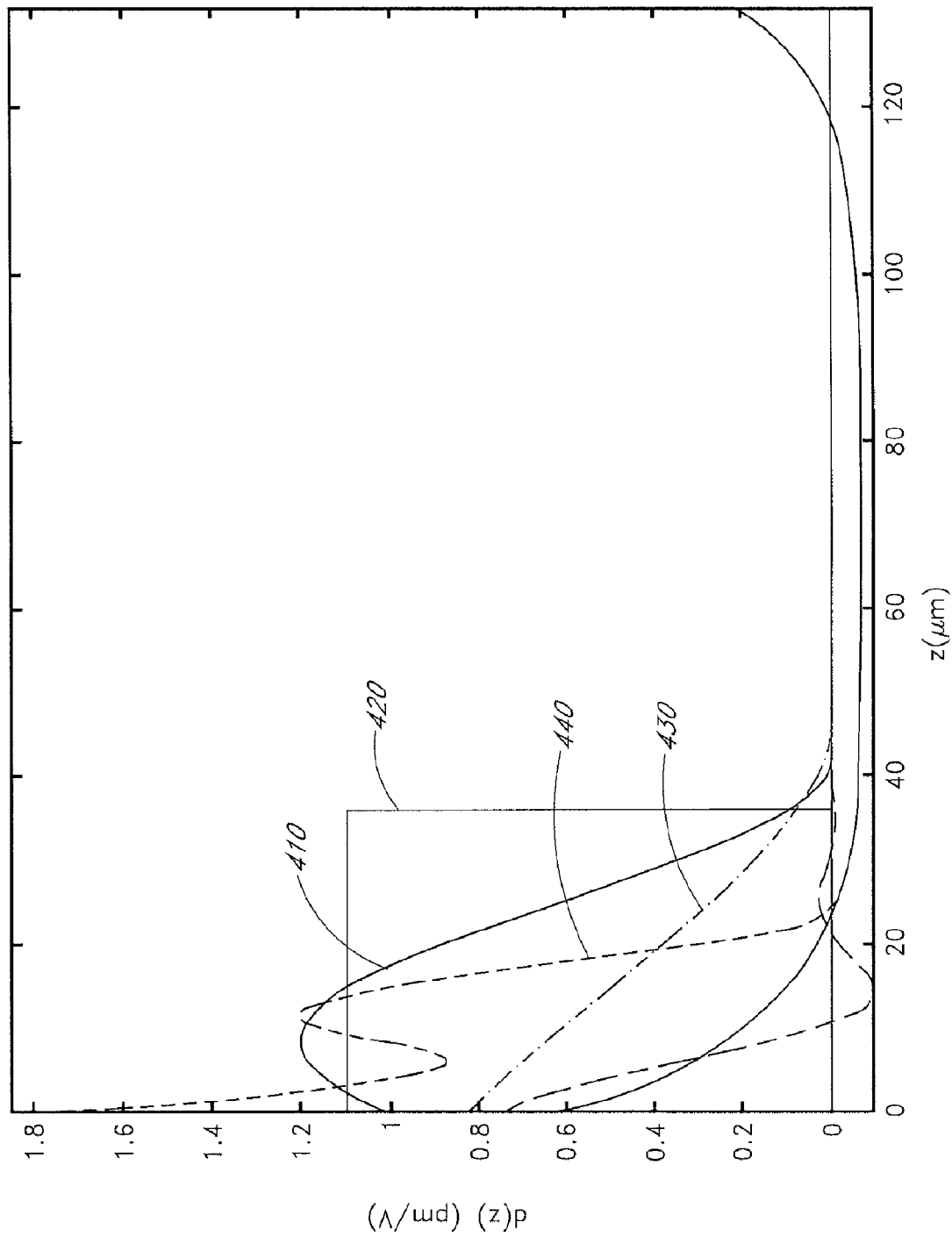
FIG. 5 illustrates graphs of a number of exemplary standard nonlinearity profile shapes.

While convergence of the method 300 has not been proved rigorously, it has been found empirically to converge to the correct solution for a wide range of profile shapes. FIG. 5 illustrates graphs of a number of exemplary standard nonlinearity profile shapes (e.g., buried Gaussian 410, rectangular profile 420, exponential 430, etc.). These nonlinearity profile shapes have been successfully retrieved by methods in accordance with embodiments described herein. With each of these nonlinearity profile shapes, the method 300 works well and recovers a nonlinearity profile that is close to the original nonlinearity profile. In fact, for the nonlinearity profile shapes of FIG. 5, the retrieved nonlinearity profiles are indistinguishable from the original nonlinearity profiles. In certain embodiments, the average error between the recovered nonlinearity profile and the original nonlinearity profile is less than approximately 0.004%. In other embodiments (e.g., for the rectangular nonlinearity profile 420), the average error between the recovered nonlinearity profile and the original nonlinearity profile is less than approximately 0.008%. Such accuracies were achieved after approximately 100 iterations, which took a few seconds on a 500-MHz computer. The exemplary nonlinearity profiles of FIG. 5 correspond generally to optical nonlinearity profiles, either measured or predicted by various theoretical models, of optically nonlinear thin films of glasses, polymers, and crystals. In particular, rectangular optical nonlinearity profiles are a common occurrence in optically nonlinear crystalline films such as $LiNbO_3$ and optically nonlinear organic materials.

The problem of retrieving an optical nonlinearity profile of a material from the sole knowledge of the MF curve of the material is analogous to the recovery of a real one-dimensional function from its Fourier transform magnitude alone. While generally, the Fourier transform magnitude is not sufficient to recover the function, in certain families of functions, the phase term of the Fourier transform can be recovered from the Fourier transform magnitude alone, and visa versa. In an exemplary family of "minimum-phase functions" (MPFs), each function is characterized by having a z-transform with all its poles and zeros on or inside the unit circle. As a result of this property, the phase of the Fourier transform and the logarithm of the Fourier transform magnitude of an MPF are the Hilbert transforms of one another. Consequently, the phase of the Fourier transform of an MPF can be recovered from the Fourier transform magnitude, such that an MPF can be reconstructed from its Fourier transform magnitude alone. This reconstruction can be performed by taking the Hilbert transform of the logarithm of the Fourier transform magnitude to obtain the phase of the Fourier transform, and then inverting the full (complex) Fourier transform to generate the MPF. However, in certain circumstances, such a direct approach is not preferable due to difficulties in its implementation (e.g., due to phase unwrapping, as described by T. F. Quatieri, Jr. and A. V. Oppenheim, "Iterative techniques for minimum phase signal reconstruction from phase or magnitude," *IEEE Trans. Aco st., Speech, Signal Processing*, Vol. 29, pp. 1187-1193 (1981)).

Iterative methods in accordance with certain embodiments described herein advantageously converge to the MPF that has a Fourier transform magnitude equal to the measured Fourier transform magnitude $|D_M(f)|$. This duality between the MPFs and the iterative methods described herein is the reason behind the agreement between the retrieved nonlinearity profiles and the corresponding original nonlinearity profiles of FIG. 5. With the exception of the rectangular nonlinearity profile, all the nonlinearity profiles in FIG. 5 are MPFs. Out of the infinite family of Fourier transform phase functions that could be associated with the measured Fourier transform magnitude, certain embodiments described herein advantageously converge to the Fourier transform phase function having the minimum phase, i.e., the MPF. This solution is unique. Thus, if it was known a priori that the nonlinearity profile to be reconstructed was an MPF, then the recovered nonlinearity profile provided by certain embodiments described herein would be certain to be the correct nonlinearity profile. Conversely, if the nonlinearity profile is not an MPF, then convergence of certain embodiments may not provide the correct nonlinearity profile. Since in general it is not known a priori whether the nonlinearity profile is an MPF or not, it is not certain that the recovered nonlinearity profile is correct.

However, in spite of this apparent limitation, computer simulations of certain embodiments described herein are observed to closely converge to the correct nonlinearity profile for a wide range of profile shapes. In certain embodiments, this close convergence is due at least in part to the fact that a large number of nonlinearity profiles are either an MPF or an approximation of an MPF.

A description of why physical functions are likely to be MPFs starts by denoting an MPF by $d_{min}(n)$, where n is an integer corresponding to sampled values of the function variable (e.g., distance z into the material having its optical nonlinearity profile analyzed). Because physical MPFs are causal (although not all causal functions are MPFs), $d_{min}(n)$ is equal to zero in at least half of the space variation (e.g., for n<0, as in the case for optical nonlinearity profiles). The energy of a MPF is defined as:

$$\sum_{n=0}^{m-1} |d_{min}(n)|^2$$

for m samples of the function $d_{min}(n)$, and satisfies the inequality:

$$\sum_{n=0}^{m-1} |d_{min}(n)|^2 \geq \sum_{n=0}^{m-1} |d(n)|^2 \qquad \text{Equation (1)}$$

for all possible values of m>0. In Equation (1), d(n) represents any of the functions that have the same Fourier transform magnitude as $d_{min}(n)$. This property suggests that most of the energy of $d_{min}(n)$ is concentrated around n=0. Stated differently, a profile with either a single peak or a dominant peak will be either an MPF or close to an MPF, and will work well with the iterative embodiments described herein.

Functions without a dominant peak can also be MPFs, but because a large number of optical nonlinearity profiles, including the most common ones, have a dominant peak, this sub-class of MPFs with dominant peaks is worth investigating. For example, the criterion of having a dominant peak is satisfied by each of the functions graphed in FIG. 5, which are all MPFs, except for the rectangular profile. Although a rectangular profile is not truly an MPF, because it has a single peak, the rectangular profile is expected to be close to an MPF. Such a rectangular profile is actually close to being an MPF because almost all of the poles and zeros of its z-transform are on or inside the unit circle, and the remaining few are just outside the unit circle. Therefore, certain embodiments of the iterative method described herein are successful in retrieving rectangular optical nonlinearity profiles (e.g., with an average error of approximately 0.008%).

In certain embodiments, a two-peak optical nonlinearity profile has a dominant peak and a secondary peak. As shown in FIG. 5, a two-peak optical nonlinearity profile 440 has a dominant peak and a secondary peak smaller than the dominant peak (e.g., the secondary peak being approximately one-third as large as the dominant peak). Such a two-peak optical nonlinearity profile 440 is expected to be an MPF. Therefore, in certain embodiments, the average error in the retrieved optical nonlinearity profile is extremely low (e.g., less than approximately $10^{-5}$%). The optical nonlinearity profile of poled silica, which typically exhibits a sharp dominant peak just below the sample's anodic surface, also satisfies the MPF criterion, thereby suggesting that embodiments of the iterative methods described herein work well for poled silica.

Figure 6:
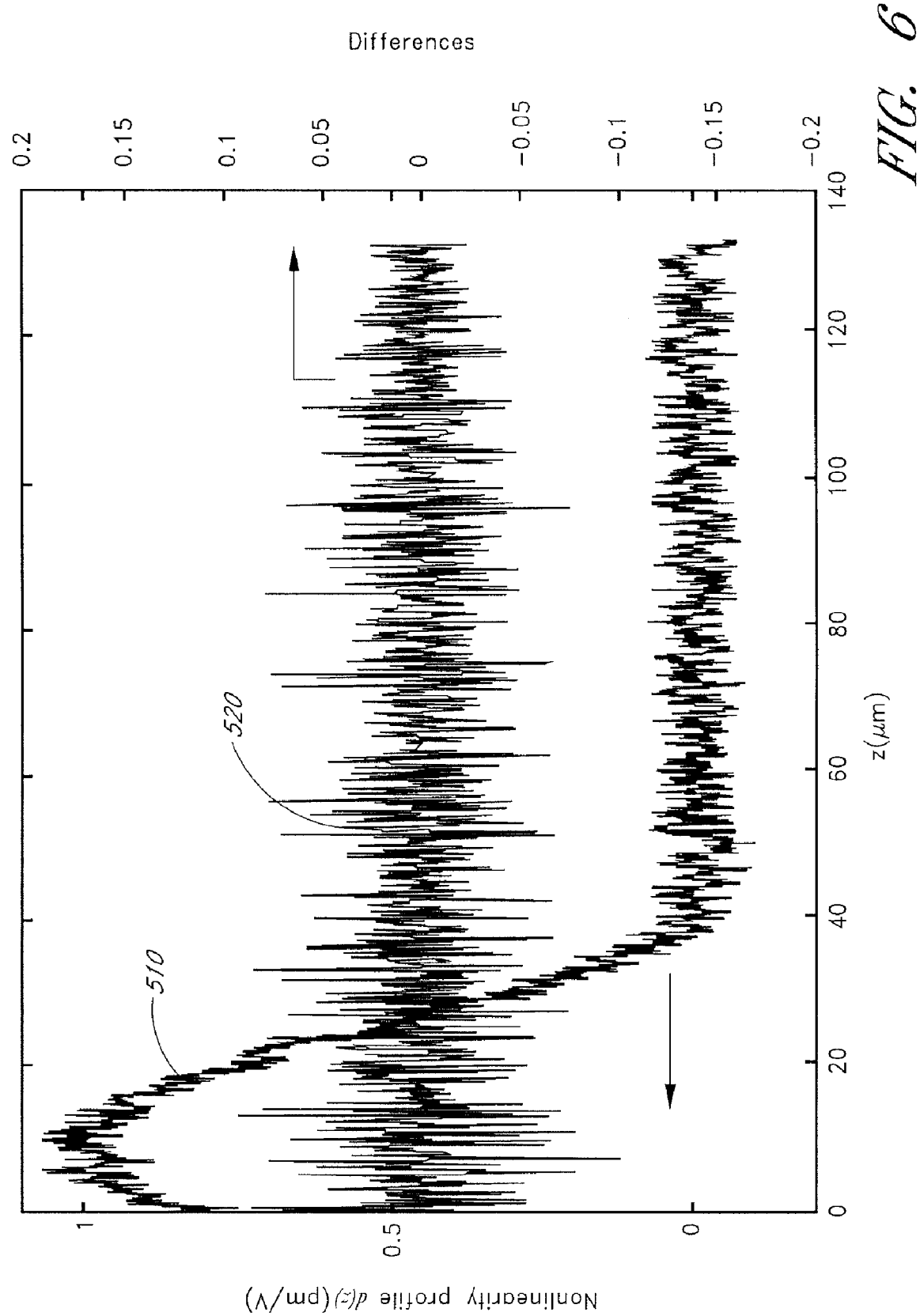
FIG. 6 illustrates a graph of results from the application of an iterative method in accordance with embodiments described herein to an embedded Gaussian nonlinearity profile.

The robustness of certain embodiments described herein is demonstrated by examining the accuracy of the iterative methods for a number of functions other than MPFs. For a first series of simulations, uniform random noise (e.g., approximately 14% peak-to-peak) was added to the optical nonlinearity profiles of FIG. 5. Such optical nonlinearity profiles are no longer MPFs. The iterative method 300 of FIG. 4 was then applied to each noisy profile, assuming an initial estimated phase term of $\exp[j\phi_E(f)]=1$. In each case, the nonlinearity profile recovered after 100 iterations was in excellent agreement with the original noisy nonlinearity profile, with an average error under approximately 1.4%. FIG. 6 illustrates graphs corresponding to such results from the application of an iterative method in accordance with embodiments described herein. FIG. 6 illustrates the exemplary noisy embedded Gaussian nonlinearity profile 510 with uniform random noise of approximately 14% peak-to-peak, with reference to the scale on the left axis. FIG. 6 also illustrates the difference 520 between the original noisy nonlinearity profile 510 and the nonlinearity profile recovered after 100 iterations, with reference to the scale on the right axis. Such results indicate that certain embodiments described herein work well even in the presence of noise.

A second series of simulations was used to investigate the iterative method on nonlinearity profiles having several peaks of comparable magnitude. Because none of the peaks of such nonlinearity profiles are dominant over the other peaks, such nonlinearity profiles do not satisfy Equation (1) and are not MPFs. For an original nonlinearity profile with two peaks of comparable magnitude, the nonlinearity profile retrieved using certain embodiments described herein is only marginally degraded and is generally acceptable. For example, when the peaks in the two-peak nonlinearity profile 440 of FIG. 5 are given comparable heights, the recovered nonlinearity profile is still essentially indistinguishable from the original nonlinearity profile, and an average difference between the original nonlinearity profile and the recovered nonlinearity profile of approximately 0.1%.

Figure 7:
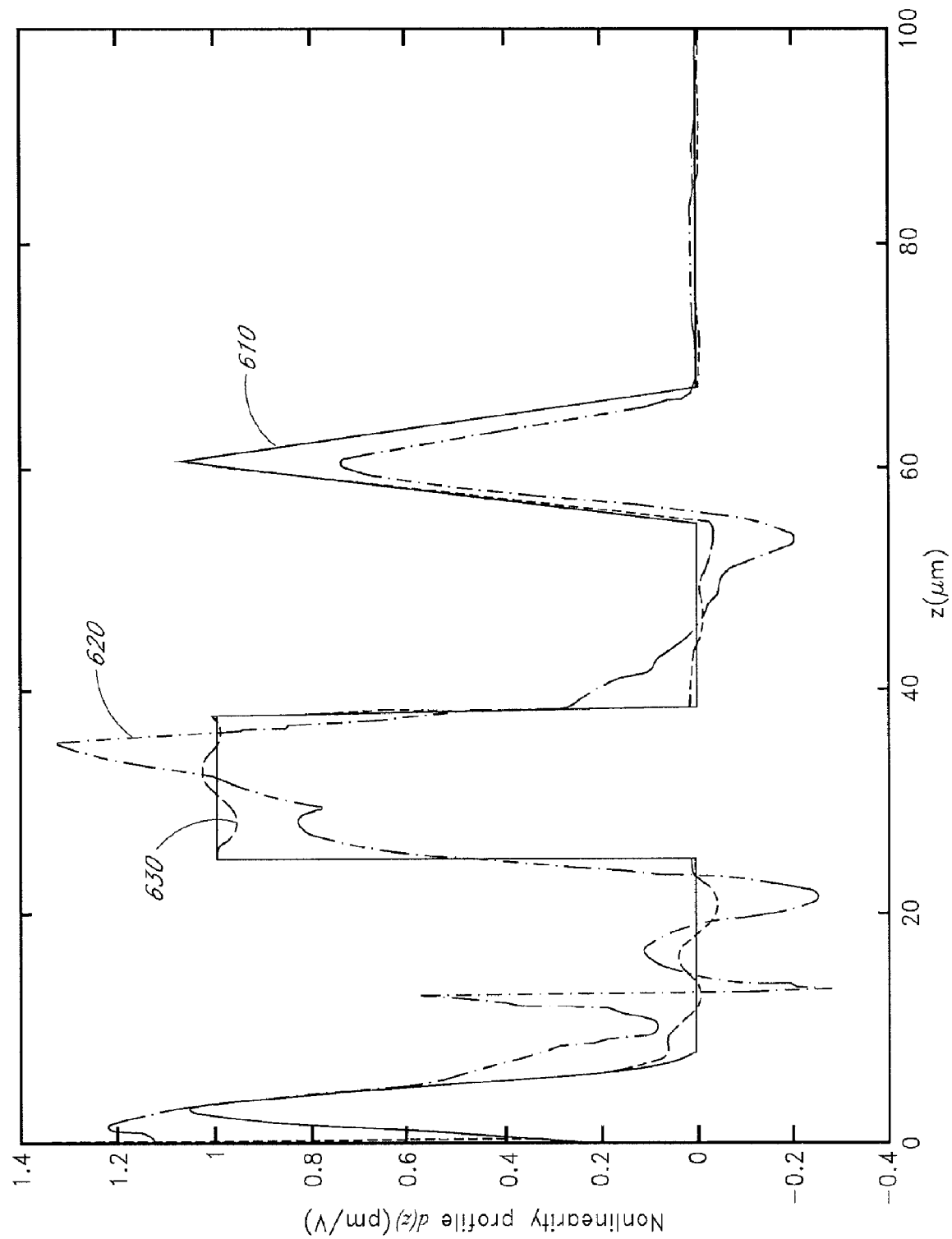
FIG. 7 illustrates a graph of an exemplary nonlinearity profile with three peaks of comparable magnitude and graphs of corresponding calculated nonlinearity profiles recovered using iterative methods in accordance with embodiments described herein.

FIG. 7 illustrates a graph of an exemplary nonlinearity profile 610 with three peaks of comparable magnitude (solid line) and graphs of two corresponding calculated nonlinearity profiles (dash-dot line 620; dotted line 630) recovered using an iterative method under differing conditions in accordance with embodiments described herein. With three peaks of comparable magnitude, as graphed in FIG. 7, the recovered nonlinearity profile 620 after 100 iterations (shown by the dash-dot line) is not nearly as accurate as in the previous examples of FIGS. 5 and 6, but it still provides a usable estimate of the original nonlinearity profile 610 (shown by the solid line). Such simulations demonstrate that certain embodiments described herein can be successfully applied to a wide range of nonlinearity profiles, including, but not limited to, MPFs.

In certain embodiments, if the nonlinearity strength at the origin $d(z=0)$ is increased to a value much larger than the rest of the nonlinearity profile (e.g., $d(z=0)=5\cdot\max\{d(z)\}$), the convergence improves substantially in terms of both accuracy and speed. Such improvement is expected because increasing the nonlinearity strength at the origin in this manner satisfies Equation (1) and the nonlinearity profile becomes an MPF, even if Equation (1) was not satisfied prior to this increase. For example, for the three-peaked nonlinearity profile 610 of FIG. 7, if $d(z=0)$ is increased to $d(z=0)=10\cdot\max\{d(z)\}$, the newly recovered nonlinearity profile 630 (shown by the dotted line) is significantly closer to the original nonlinearity profile 610 (shown by the solid line) than was the recovered nonlinearity profile 620 prior to the increase (shown by the dash-dot line). In certain embodiments, increasing the nonlinearity strength at the origin opens the possibility of recovering any nonlinearity profile by depositing the material onto a stronger and very thin optically nonlinear material (e.g., $LiNbO_3$). The thinness of the optically nonlinear material does not affect convergence, but it does make it easier to deposit the material and to measure its MF curve.

There are two minor limitations to the iterative methods of certain embodiments described herein. A first limitation is that the exact location (e.g., how deeply $d(z)$ is buried below the surface) of the nonlinearity profile within the material is not recoverable. A second limitation is that the sign of the nonlinearity profile is not unequivocally determined. Consequently, if $d(z)$ is a solution provided by an iterative method described herein for a given optically nonlinear sample, then all $\pm d(z-z_0)$ functions are also solutions. However, in certain embodiments, these limitations are fairly inconsequential because it is significantly more important to determine the shape of the nonlinearity profile than to determine the sign or exact location of the nonlinearity profile. Furthermore, the sign and the exact location of the nonlinearity profile can be determined by other methods (e.g., by using the reference-sample IFT technique).

To illustrate the applicability of embodiments described herein, the iterative method was applied to an optically nonlinear material, namely a wafer of poled silica. A 25×25×0.15 millimeter wafer of fused silica (Infrasil) was thermally poled in air at approximately 270 degrees Celsius and with an applied voltage of 4.8 kilovolts for 15 minutes. The MF spectrum (which is proportional to the Fourier transform magnitude of the nonlinearity profile) was measured from the wafer, and is graphed in FIG. 8 as open circles. The iterative method 300 of FIG. 4 was used, assuming an initial phase term of $\exp[j\phi_E(f)]=1$ and using the measured MF spectrum as the measured Fourier transform magnitude of the nonlinearity profile, to recover a first nonlinearity profile. The same wafer was also characterized by the two-sample IFT technique, which provided a second, absolute nonlinearity profile.

Figure 9:
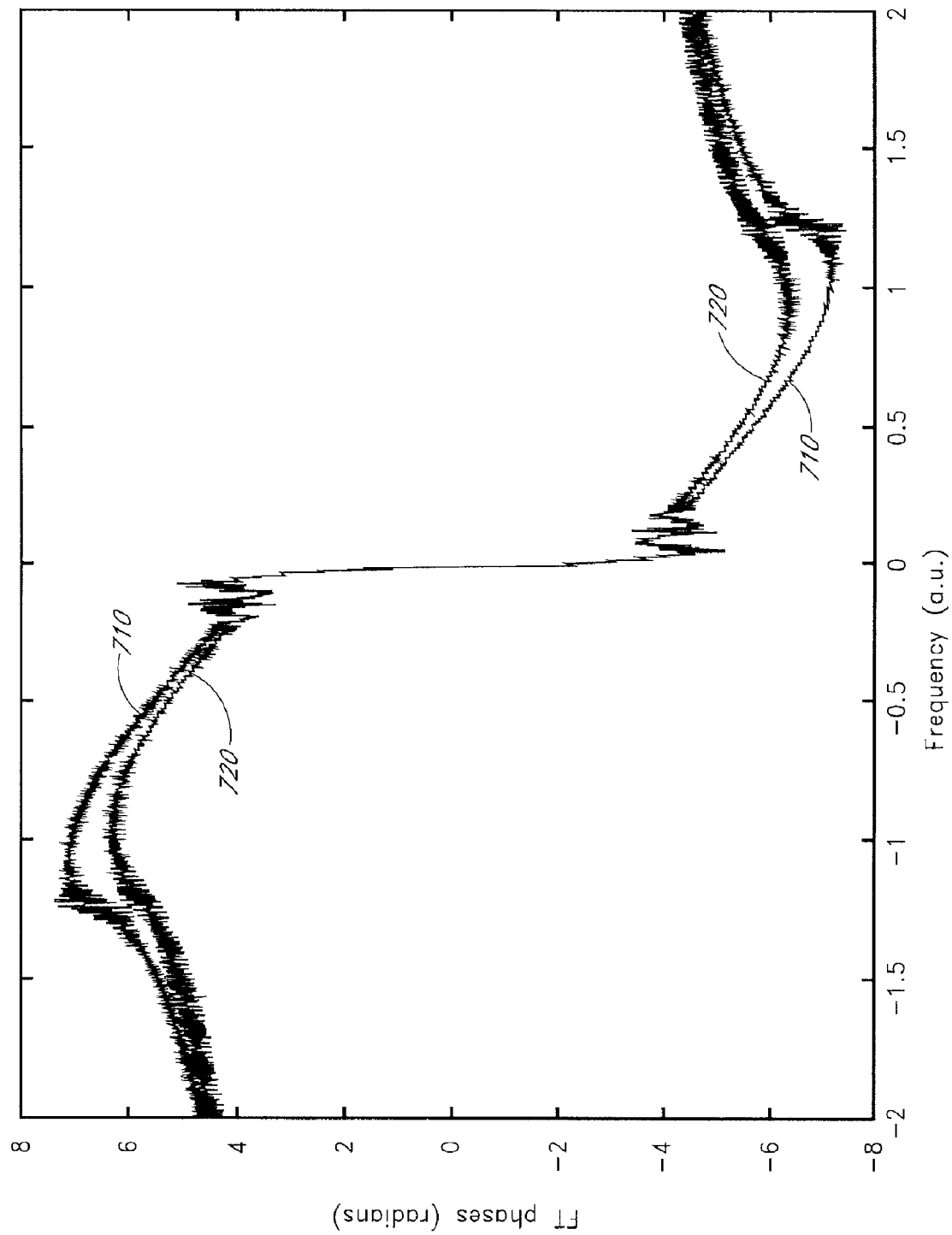
FIG. 9 illustrates a graph of the phase of the Fourier transform of the nonlinearity profile obtained from an iterative method and a graph of the phase of the Fourier transform of the nonlinearity profile obtained from the two-sample IFT technique.
Figure 10:
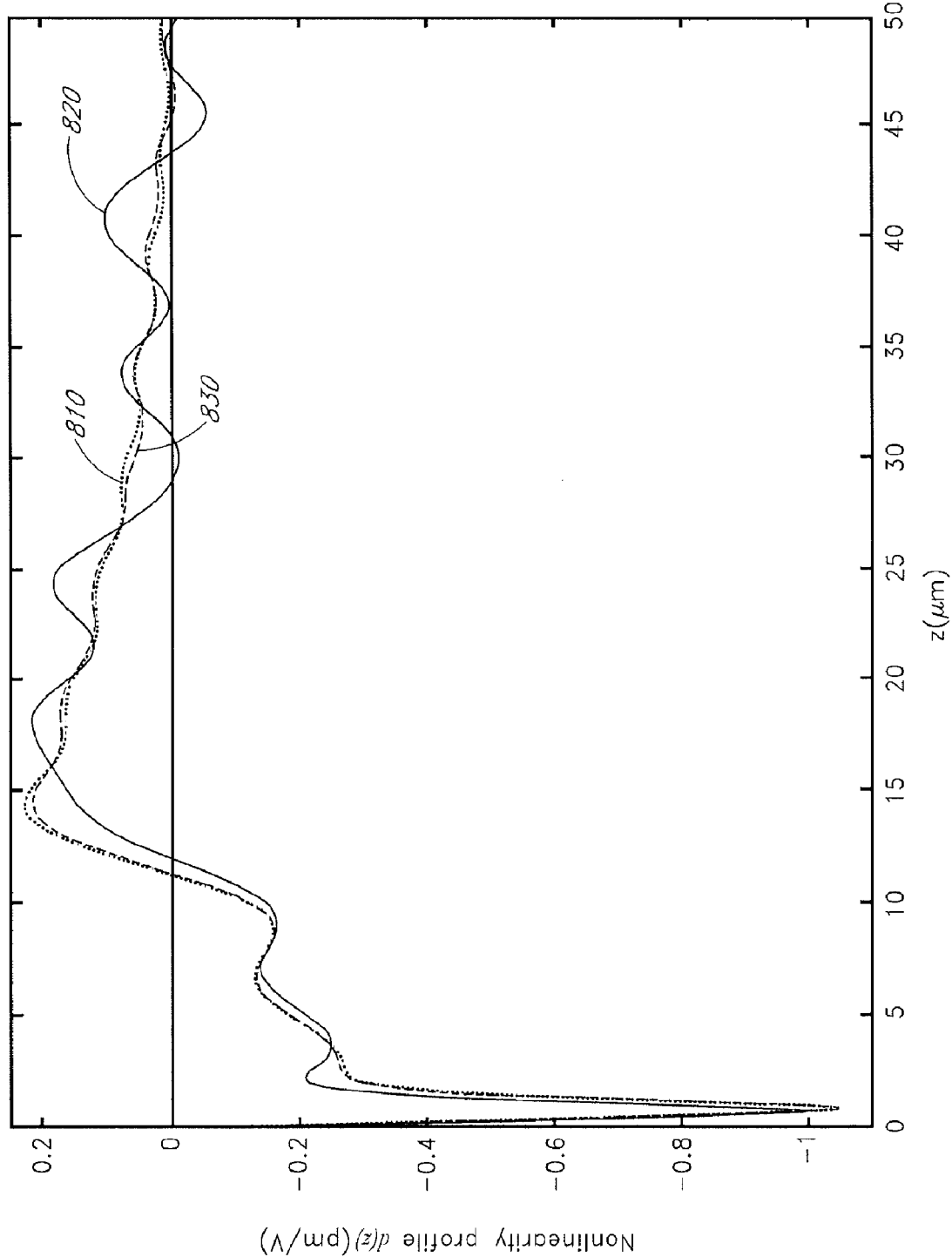
FIG. 10 illustrates graphs of the nonlinearity profiles obtained from an iterative method and from the two-sample IFT technique.

FIG. 9 illustrates a graph 710 of the phase of the Fourier transform of the nonlinearity profile obtained from the iterative method and a graph 720 of the phase of the Fourier transform of the nonlinearity profile obtained from the two-sample IFT technique. FIG. 10 illustrates a graph 810 of the nonlinearity profile obtained from the iterative post-processing method (dotted line) using an initial estimated phase term of $\exp[j\phi_E(f)]=1$, and a graph 820 of the nonlinearity profile obtained from the two-sample IFT technique (solid line). The two nonlinearity profiles of FIG. 10 are in excellent agreement, with both nonlinearity profiles exhibiting a sharp nonlinearity coefficient peak with a magnitude of approximately $d_{33}=-1$ picometer/volt (pm/V) just below the surface of the wafer, a sign reversal at a depth of approximately 12 microns, and a wider positive nonlinear region extending to a depth of approximately 45 microns. These observations are in accordance with other nonlinearity profiles obtained by other IFT techniques in similarly poled samples. As shown in FIG. 9, the Fourier transform phase spectra recovered by these two techniques are also in very good agreement with each other. The agreement between the results of these two very different techniques lends support to both the iterative processing method and the two-sample IFT technique.

Figure 8:
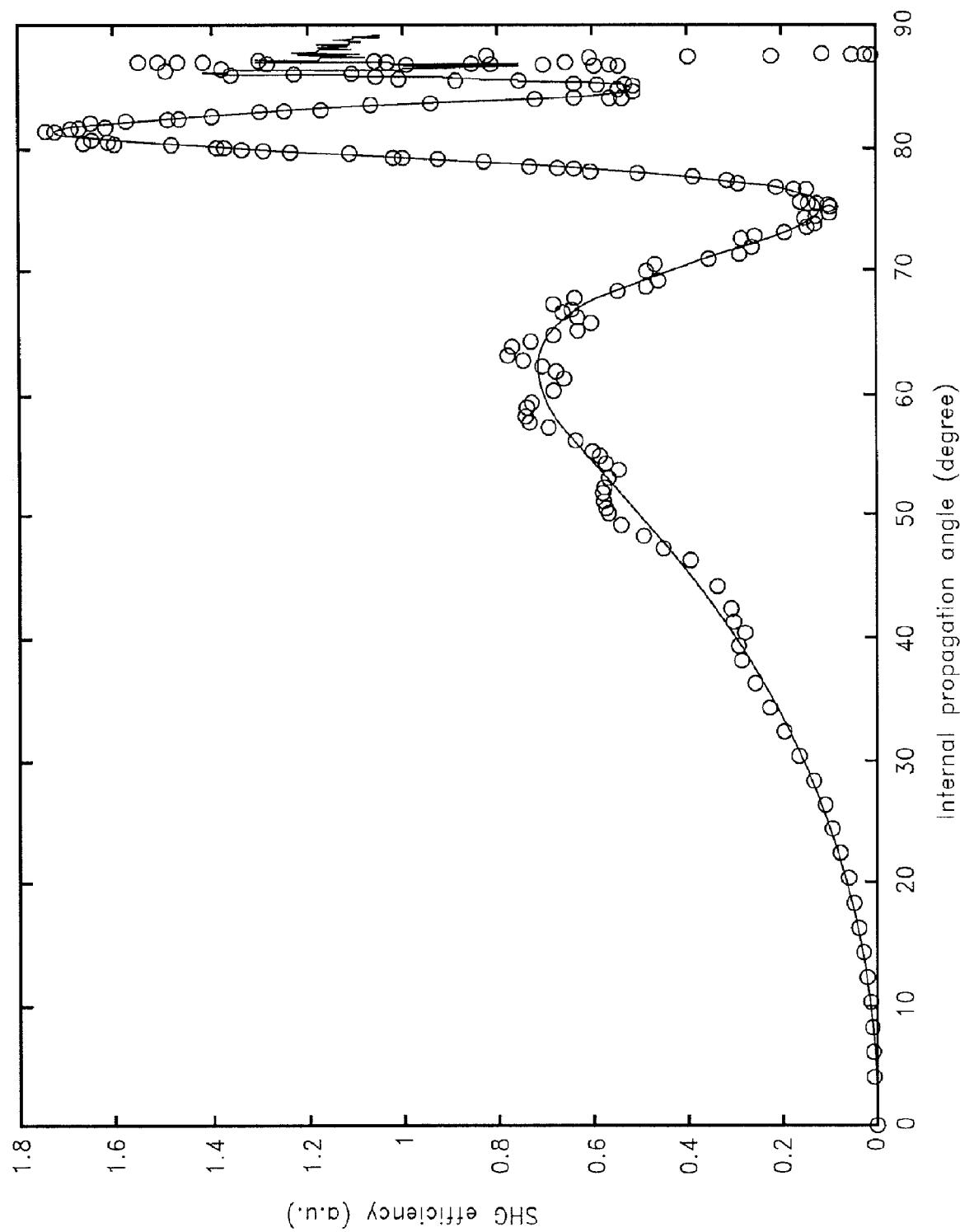
FIG. 8 illustrates a graph of the measured Maker fringe spectrum from a poled silica wafer and a graph of the calculated Maker fringe spectrum after post-processing of the nonlinearity profile.

To investigate the effects of using an initial phase term $\exp[j\phi_E(f)]\neq 1$, the iterative method was performed using the phase of the Fourier transform of the two-sample IFT technique as a better initial guess for the phase. Such an operation is equivalent to using the iterative method to post-process the phase of the Fourier transform recovered by the IFT technique, with the goal of obtaining an even more accurate nonlinearity profile. FIG. 10 shows the nonlinearity profile 830 (dash-dot line) obtained after 100 iterations of the iterative method with the initial phase term from the two-sample IFT technique. Comparison to the nonlinearity profile 820 (solid line) obtained from the two-sample IFT technique shows that the post-processing did not modify the overall profile shape, but that it significantly smoothed out the artificial oscillations introduced by the IFT technique. The two nonlinearity profiles obtained from the iterative method using the initial phase term of $\exp[j\phi_E(f)]=1$ (dotted line 810) and from the iterative method using the initial phase term from the two-sample IFT technique (dash-dot line 830) are very close to each other. The average difference between these two nonlinearity profiles is approximately 0.14%, which demonstrates the validity of both approaches. The similarity between the two nonlinearity profiles before and after post-processing confirms that the IFT technique comes very close to recovering the actual nonlinearity profile. It also demonstrates the usefulness of the iterative method in the application of post-processing a nonlinearity profile obtained by an IFT technique. To illustrate the utility of this post-processing technique, FIG. 8 shows the MF spectrum (solid line) derived numerically from the post-processed nonlinearity profile, which agrees quite well with the measured MF spectrum (open circles).

Figure 11A:
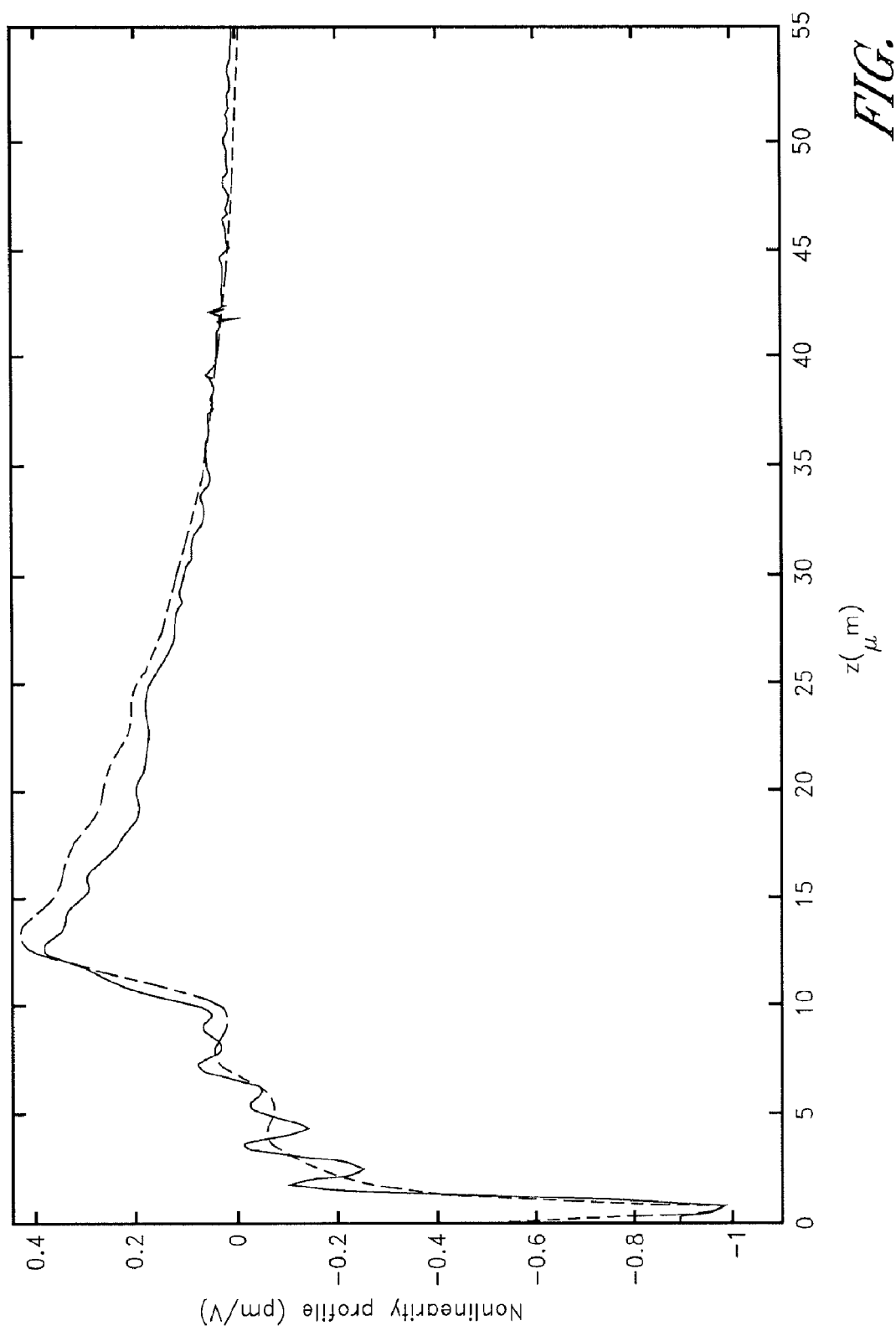
FIG. 11A illustrates a plot of the nonlinearity profile of a poled silica wafer before applying the iterative method (solid line) and a plot of the nonlinearity profile after applying the iterative method (dashed line).
Figure 11B:
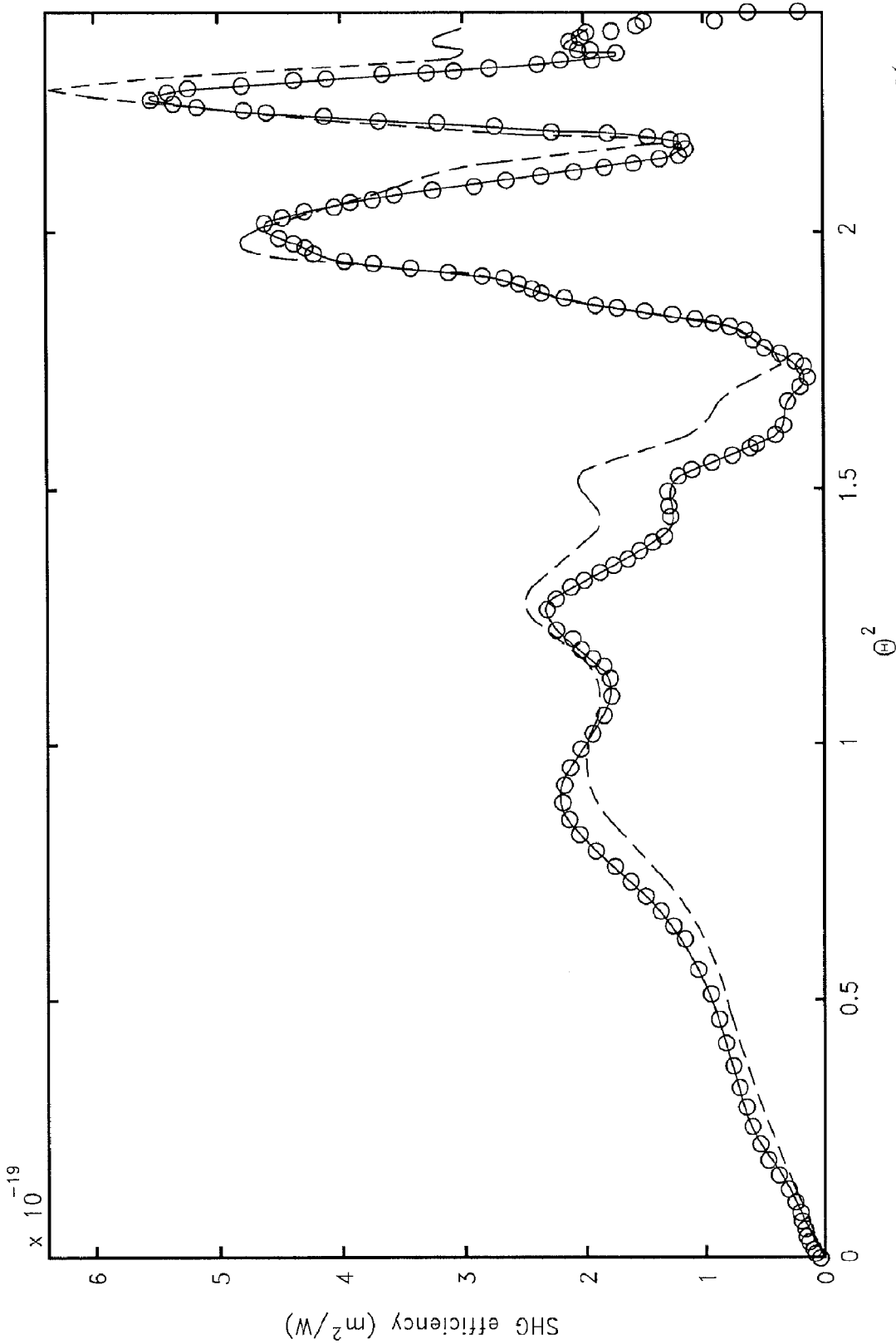
FIG. 11B illustrates a plot of the measured Maker fringe spectrum of the poled silica wafer (closed circles), a plot of the theoretical Maker fringe spectrum (dashed line) before applying the iterative method, and a plot of the calculated Maker fringe spectrum (solid line) after applying the iterative method.

FIG. 11A illustrates a graph of an initial nonlinearity profile (solid line) measured from a fused-silica wafer (Infrasil, 25×25×1 millimeter) which was thermally poled at approximately 270 degrees Celsius and with an applied voltage of 5 kV for 15 minutes. The measured MF spectrum was obtained using a cylinder-assisted technique that utilizes two half-cylinders to avoid total internal reflection at the back of the silica wafer. This cylinder-assisted technique is more fully disclosed by A. Ozcan et al., "Cylinder-Assisted Maker-Fringe Technique," *Electronics Letters*, Vol. 39, pp. 1834-1836 (2003). The measured MF curve of this poled sample is shown in FIG. 11B as the closed circles. An IFT technique, as described by U.S. patent application Ser. Nos. 10/357,275, 10/378,591, and 10/645,331, was used to retrieve the initial nonlinearity profile shown in FIG. 11A. The calculated MF curve corresponding to the initial nonlinearity profile is shown in FIG. 11B as a dashed line. After 100 iterations of the post-processing method in accordance with embodiments described herein (which took only about 1 minute for 213 data points), the corrected nonlinearity profile (shown in FIG. 11A as a dashed line) is obtained. The artificial oscillations in the initial nonlinearity profile, which originated from practical limitations in the IFT technique, have been significantly smoothed out by the post-processing method. Furthermore, the calculated MF curve (solid line of FIG. 11B) of this corrected nonlinearity profile agrees more closely with the measured MF curve (closed circles of FIG. 11B) than does the calculated MF curve (dashed line of FIG. 11B) before the application of the post-processing method. This agreement provides a measure of the substantial accuracy improvement that can be obtained with this simple technique.

Certain embodiments of the iterative post-processing technique described herein advantageously provide significant attenuation of artificial oscillations in the nonlinearity profiles, as demonstrated by testing the post-processing technique with other IFT techniques. Therefore, certain embodiments of the iterative post-processing technique are a powerful tool to improve the accuracy of nonlinearity profiles recovered by an IFT technique. Certain embodiments of such post-processing are also advantageously fast. For example, on a 500-MHz computer, 100 iterations typically take only approximately 10 seconds, as compared to about 5-10 minutes for the data processing of an IFT technique. In addition, the iterative method converges much faster if the thickness W of the optically nonlinear region of the material is known. Once this thickness W is known, the values of d(z) can be set to zero over the z<0 space and over the z>W space, thereby restricting the range of z values over which d(z) is unknown. Certain such embodiments do not need to recover as many discrete values of d(z), so convergence is achieved more quickly.

In certain embodiments, the iterative methods described herein advantageously enable the accurate recovery of the missing phase information of the Fourier transform of the nonlinearity profile and of the nonlinearity profile itself. In certain embodiments, the methods described herein advantageously provide a substantial improvement over prior art IFT techniques because of the simplicity of both the measurement and the computer code which performs the methods. In certain embodiments, the methods described herein advantageously provide a greater speed of data processing than do prior art IFT techniques. In certain embodiments, the methods described herein advantageously provide nonlinearity profiles with reduced errors as compared to those from prior art IFT techniques. When applied to poled silica samples, certain embodiments of the methods described herein lead to nonlinearity profiles that are in excellent agreement with the nonlinearity profiles obtained using more absolute IFT techniques. In addition, in certain embodiments, the iterative post-processing methods described herein are advantageously used to improve the accuracy of the nonlinearity profiles obtained using an IFT technique.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A method of estimating a nonlinearity profile of a material, the method comprising:
 (a) providing a magnitude of a transform of a measured nonlinearity profile measured from the material;
 (b) providing an estimated phase term of the transform of the measured nonlinearity profile;
 (c) multiplying the magnitude and the estimated phase term to generate an estimated transform;
 (d) calculating an inverse transform of the estimated transform; and
 (e) calculating a real component of the inverse transform to generate an estimated nonlinearity profile.

2. The method of claim 1, further comprising:
 (f) calculating a transform of the estimated nonlinearity profile; and
 (g) calculating a calculated phase term of the transform of the estimated nonlinearity profile.

3. The method of claim 2, further comprising:
 (h) using the calculated phase term of (g) as the estimated phase term of
 (c) and repeating (c)-(e).

4. The method of claim 3, wherein (c)-(h) are iteratively repeated until the estimated nonlinearity profile reaches convergence.

5. The method of claim 4, wherein convergence is reached when an average difference between estimated nonlinearity profiles obtained after two consecutive iterations is less than a predetermined value.

6. The method of claim 5, wherein the predetermined value is 1% of the estimated nonlinearity profile of an iteration.

7. The method of claim 3, wherein (c)-(h) are iteratively repeated a predetermined number of times.

8. The method of claim 1, wherein providing the magnitude of the transform of the measured nonlinearity profile comprises measuring a Maker fringe spectrum of the material.

9. The method of claim 1, wherein providing the magnitude of the transform of the measured nonlinearity profile comprises providing a previously-measured Maker fringe spectrum of the material.

10. The method of claim 1, wherein providing the magnitude of the transform of the measured nonlinearity profile comprises:
measuring the nonlinearity profile of the material; and
calculating the magnitude of the transform of the measured nonlinearity profile.

11. The method of claim 1, wherein providing the estimated phase term of the transform of the measured nonlinearity profile comprises providing an initial estimated phase term equal to one.

12. The method of claim 1, wherein providing the estimated phase term of the transform of the measured nonlinearity profile comprises providing an initial estimated phase term equal to a measured phase term of the transform of the measured nonlinearity profile.

13. The method of claim 1, wherein the estimated nonlinearity profile is a real and causal function.

14. The method of claim 1, wherein the nonlinearity profile is a minimum-phase function.

15. The method of claim 1, wherein the material comprises a thin film.

16. The method of claim 1, wherein the material comprises poled silica.

17. The method of claim 1, further comprising using the estimated nonlinearity profile to provide information regarding the nonlinearity profile of the material.

18. The method of claim 17, wherein using the estimated nonlinearity profile to provide information regarding the nonlinearity profile of the material comprises displaying a portion of the estimated nonlinearity profile.

19. The method of claim 18, wherein the portion of the estimated nonlinearity profile is displayed as a graph of nonlinearity as a function of depth below a surface of the material.

20. The method of claim 18, wherein the transform of the measured nonlinearity profile is a Fourier transform of the measured nonlinearity profile.

21. A method of improving the accuracy of a measured nonlinearity profile of a material, the method comprising
(a) providing the measured nonlinearity profile of the material;
(b) calculating a magnitude of a transform of the measured nonlinearity profile;
(c) providing an estimated phase term of the transform of the measured nonlinearity profile;
(d) multiplying the magnitude and the estimated phase term to generate an estimated transform;
(e) calculating an inverse transform of the estimated transform;
(f) calculating a real component of the inverse transform to generate an estimated nonlinearity profile;
(g) calculating a transform of the estimated nonlinearity profile;
(h) calculating a calculated phase term of the transform of the estimated nonlinearity profile;
(i) using the calculated phase term of (h) as the estimated phase term of (d); and
(j) iteratively repeating (d)-(i) until the estimated nonlinearity profile reaches convergence.

22. The method of claim 21, further comprising using the estimated nonlinearity profile to provide information regarding the measured nonlinearity profile of the material.

23. The method of claim 22, wherein using the estimated nonlinearity profile to provide information regarding the measured nonlinearity profile of the material comprises displaying a portion of the estimated nonlinearity profile.

24. The method of claim 23, wherein the portion of the estimated nonlinearity profile is displayed as a graph of nonlinearity as a function of depth below a surface of the material.

25. The method of claim 23, wherein the transform of the measured nonlinearity profile is a Fourier transform of the measured nonlinearity profile.

26. A computer-readable medium having instructions stored thereon which cause a general-purpose computer to perform a method of estimating a nonlinearity profile of a material, the method comprising:
estimating an estimated phase term of a transform of a measured nonlinearity profile measured from the material;
multiplying a magnitude of the transform of a measured nonlinearity profile measured from the material and the estimated phase term to generate an estimated transform;
calculating an inverse transform of the estimated transform; and
calculating a real component of the inverse transform to generate an estimated nonlinearity profile.

27. The computer-readable medium of claim 26, wherein the method further comprises using the estimated nonlinearity profile to provide information regarding the nonlinearity profile of the material.

28. The computer-readable medium of claim 27, wherein using the estimated nonlinearity profile to provide information regarding the nonlinearity profile of the material comprises displaying a portion of the estimated nonlinearity profile.

29. The computer-readable medium of claim 28, wherein the portion of the estimated nonlinearity profile is displayed as a graph of nonlinearity as a function of depth below a surface of the material.

30. The computer-readable medium of claim 27, wherein the transform of the measured nonlinearity profile is a Fourier transform of the measured nonlinearity profile.

31. A computer system comprising:
means for estimating an estimated phase term of a transform of a measured nonlinearity profile measured from the material;
means for multiplying a magnitude of the transform of a measured nonlinearity profile measured from the material and the estimated phase term to generate an estimated transform;
means for calculating an inverse transform of the estimated transform; and
means for calculating a real component of the inverse transform to generate an estimated nonlinearity profile.

32. The computer system of claim 31, further comprising means for using the estimated nonlinearity profile to provide information regarding the nonlinearity profile of the material.

33. The computer system of claim 32, wherein the means for using the estimated nonlinearity profile to provide information regarding the nonlinearity profile of the material comprises a display which displays a portion of the estimated nonlinearity profile.

34. The computer system of claim 33, wherein the portion of the estimated nonlinearity profile is displayed as a graph of nonlinearity as a function of depth below a surface of the material.

35. The computer system of claim 32, wherein the transform of the measured nonlinearity profile is a Fourier transform of the measured nonlinearity profile.

* * * * *

UNITED STATES PATENT AND TRADEMARK OFFICE
CERTIFICATE OF CORRECTION

PATENT NO. : 7,417,742 B2  Page 1 of 1
APPLICATION NO. : 11/841587
DATED : August 26, 2008
INVENTOR(S) : Ozcan et al.

It is certified that error appears in the above-identified patent and that said Letters Patent is hereby corrected as shown below:

On the title page, item [54] and column 1, line 2: after "NONLINEARITY" add -- PROFILE --.

Title page 1, item [75] (Inventors), line 2, delete "Diggonet" and insert -- Digonnet --, therefor.

Title page 1, item [75] (Inventors), line 3, delete "Kingo" and insert -- Kino --, therefor.

Title page 1, item [73] (Assignee), line 1, delete "Trustess" and insert -- Trustees --, therefor.

Title page 2, item [56] column 2, line 34, delete "2002," and insert -- 2003, --, therefor.

Title page 2, item [56] column 2, line 40, after "©" insert -- 2004 --, therefor.

Title page 2, item [56] column 2, line 57, delete "l.," and insert -- al., --, therefor.

Column 7, line 39, delete "Aco st.," and insert -- Acoust., --, therefor.

Column 13, line 38, in Claim 21, after "comprising" insert -- : --, therefor.

Signed and Sealed this

Thirty-first Day of March, 2009

JOHN DOLL
*Acting Director of the United States Patent and Trademark Office*